United States Patent [19]

Fukusaki et al.

[11] Patent Number: 5,213,975
[45] Date of Patent: May 25, 1993

[54] METHODS OF PREPARING OPTICALLY ACTIVE EPOXY ALCOHOL

[75] Inventors: Eiichiro Fukusaki; Hiroshi Takahama; Minako Hada; Yasuyuki Kimura; Hiroyuki Yuasa; Yutaka Nakazono; Shuji Senda; Tetsuo Omata, all of Osaka, Japan

[73] Assignee: Nitto Denko Co., Ltd., Ibarake, Japan

[21] Appl. No.: 783,448

[22] Filed: Oct. 24, 1991

[30] Foreign Application Priority Data

Oct. 30, 1990 [JP] Japan .................. 2-294486
Jun. 14, 1991 [JP] Japan .................. 3-170625

[51] Int. Cl.$^5$ .................. C12P 17/02; C12N 9/20; C07P 41/00
[52] U.S. Cl. .................. 435/123; 435/198; 435/280
[58] Field of Search .................. 435/123, 280, 198

[56] References Cited

U.S. PATENT DOCUMENTS

| | | |
|---|---|---|
| 4,732,853 | 3/1988 | Whitesides et al. ............ 435/123 |
| 4,923,810 | 5/1990 | Walts et al. ............ 435/123 |
| 4,996,158 | 2/1991 | Oda et al. ............ 435/280 |

FOREIGN PATENT DOCUMENTS

| | | |
|---|---|---|
| 0345658 | 2/1989 | European Pat. Off. . |
| 0357009 | 3/1989 | European Pat. Off. . |
| 0344791 | 4/1989 | European Pat. Off. . |
| 0333142 | 9/1989 | European Pat. Off. ............ 435/123 |
| 0343714 | 11/1989 | European Pat. Off. ............ 435/123 |
| 1235599 | 5/1989 | Japan . |

OTHER PUBLICATIONS

Biotech Abs. 91-194871/27 Nitto Denko Co. Fukusaki et al EP-435293 Jul. 1991.
J Am. Chem Soc. 1984, 106, 7250-7251, Ladner et al.
Tetrahedron Letters, vol. 29, No. 20, pp. 2455-2548, 1988, Bianchi et al.
Chem. Abstract, vol. 112, No. 19, May 7, 1990, No. 177061 Aniano, Masita et al.

Primary Examiner—Herbert J. Lilling
Attorney, Agent, or Firm—Joseph C. Mason, Jr.; Ronald E. Smith

[57] ABSTRACT

This invention relates to the methods of preparing optically active epoxy alcohol which is caracterized by the steps of adding carboxylic anhydride to racemic epoxy alcohol (formula 1) in the presence of a hydrolase in an organic solvent, esterifying (−)-form of the epoxy alcohol preferentially to be epoxy ester (formula 2), separating optically active epoxy ester (formula 2) from optically active epoxy alcohol (formula 3) to yield optically active epoxy alcohol (formula 4), so that epoxy alcohol (formula 1) in high purity can be obtained easily and safely at ordinary temperature.

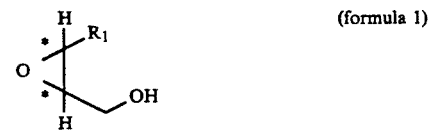

(formula 1)

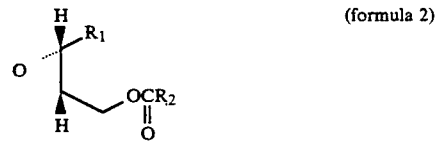

(formula 2)

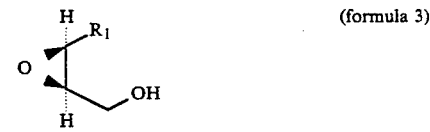

(formula 3)

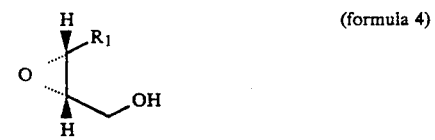

(formula 4)

5 Claims, 12 Drawing Sheets

METHODS OF PREPARING OPTICALLY ACTIVE EPOXY ALCOHOL

BACKGROUND OF THE INVENTION

The optically active substance of epoxy alcohol (formula 1) is noted as a synthetic intermediate of medicines, pesticides, and biologically active substances.

Especially, the (−)optically active substance of 2,3-epoxy-8-methyl-1-nonanol is an important constituent of sex pheromone of Lymantria dispar L.

(formula 1)

Here, $R_1$ and $R_2$ denote straight-chain or branched alkyl groups containing 1 through 20 carbon atoms.

1. Industrial Field of the Invention

The present invention relates to the methods of preparing optically active epoxy alcohol and an intermediate prepared in the process. The objective of the invention is to provide the preparation of epoxy alcohol, which readily, selectively, and efficiently yields optically active epoxy alcohol is a useful synthetic intermediate of medicines, pesticides, biologically active substances such as sex pheromone of Lymantria dispar L.

2. Description of Prior Art

Synthesis of epoxy alcohol (formula 1) has been proposed by Katsuki K. (J.Am. Chem. Soc. 1980, vol 102; 5,974) which utilizes asymmetric epoxidation of allyl alcohol.

This methods is, however, not practical; since
(1) it requires an expensive asymmetric reducing agent;
(2) the temperature is to be controlled to below −50° C.; and
(3) it requires dangerous agents such as t-butyl hydroperoxide.

Another known method proposed by Daniel Bianchi (tetraheron Letter, 29 (20) 2455 to 2458, 88) is to synthesize the optically active substance of epoxy alcohol (formula 1) by means of asymmetric transesterification of epoxy alcohol (formula 1) and acetates with lipase.

The method also has some drawbacks to be practical such as low optical purity and poor yield.

DETAILED DESCRIPTION OF THE INVENTION

Hereinafter, this inventional embodiments are discribed in detail.

The racemic epoxy alcohol (formula 1), the starting material in this invention, is easily obtained or prepared.

For example, it is showed the method that allyl alcohol (formula 7) is reacted with the vanadyl acetylacetonato and t-butyl hydoroperoxide.

(formula 7)

Here, $R_1$ and $R_2$ denote straight-chain or branched alkyl groups containing 1 through 20 carbon atoms.

Among the embodiments of the epoxy alcohol, especially the (−)optically active substance of 2,3-epoxy-8-methyl-1-nonanol is useful as the synthetic intermediate of sex pheromone for injurious insects in forests (Lymantria dispar L.).

That is, the Lymantria dispar L. is prepared from (−)-(2S, 3R)-2,3-expoxy-8-methyl-1-nonanol by the methods of K. Mori and others (Tetrahedron; vol.42, 3471 (1986)).

In this invention, the carboxylic anhydride is added to the epoxy alcohol (formula 1) in the presence of a hydrolase in an organic solvent so as to acylate (−)optically active substance of epoxy alcohol preferentially to be optically active epoxy ester (formula 2).

(formula 2)

Here, $R_1$ and $R_2$ denote straight-chain or branched alkyl groups containing 1 through 20 carbon atoms.

In this raction, the enzyme to be used is a lipase like a lipase derived from pancrea of pig, yeast, mold, and a esterase like a esterase derived from lever of pig, a cholesterolesterase.

Either purified or crude enzymes can be used, and the state of enzymes is not any restriction, therefore it is to be favorably used any state of powder, grain, or dried biomass microorganism (treateted biomass and paused biomass) contained the enzyme etc.

These enzymes are possible to be used as it is, or as immobilizing on carrier.

Moreover, after this reaction, it is possible to re-use the recovered enzymes.

The organic solvent favorably used in this reaction is all of non-aqueous system solvents, for example an acyclic hydrocarbon solvent like as n-hexane, n-heptane, n-octane, isobutane, isopentane, isooctane, and a cyclic hydrocarbon solvent like as cyclopentane, cyclohexane, and a halogenated hydrocarbon solvent like as dichloromethane, trichloromethane, and an aromatic hydrocarbon solvent like as benzene, toluene, xylene, and an ether group solvent like as diethylether, diisopropylether, n-butylether, tetrahydrofuran, tetrahydropyran and carbon tetrachloride etc.

All of the carboxylic acids to be substrate for hydroalse can be used, and more favorably used acyclic carboxylic acids are carbon number in the range of 2 to 10 or cyclic carboxylic acids are carbon number in the range of 4 to 10.

The example of acyclic carboxylic acids is acetate, propyonic acid, butylic acid, valeric acid or capronic acid etc., and cyclic carboxylic acid anhydrides like as succinic anhydride, maleic anhydride and glutaric anhydride etc.

The combination ratio of racemic epoxy alcohol (formula 1) and acyl group donator (carboxylic anhydride) is 1: not less than 0.5 in mole ratio.

The reaction temperature in this reaction is preferably within active temperature for enzyme, and ordinary it is the range of 10° C. to 50° C.

The obtained optically active (−)-epoxy ester (formula 2) is new epoxy ester and oily materials at room temperature.

After the asymmetric hydrolize reaction, optically active (−)-epoxy ester (formula 2) and optically active (+)-epoxy alcohol (formula 3) are separated from the reaction mixture.

(formula 3)

Here, $R_1$ and $R_2$ denote straight-chain or branched alkyl groups containing 1 through 20 carbon atoms.

As for examples of this separating process, there are extraction by using organic solvent being slightly soluble in water, two solvents of insoluble organic solvent and water as two layers system and distillaction, etc.

Moreover, the obtained optically active (−)-epoxy ester (formula 2) in this separation can be easily converted into optically active (−)-epoxy alcohol (formula 4) by hydrolyzing with alkali like pottasium hydroxide, etc.

(formula 4)

Here, $R_1$ and $R_2$ denote straight-chain or branched alkyl groups containing 1 through 20 carbon atoms.

As described above, in this invention, optically active (+)-epoxy alcohol (formula 3) and optically active (−)-epoxy alcohol (formula 4) are obtained.

Hereinafter, the methods of preparing optically active epoxy alcohol from the intermediate in above-mentioned methods, that is, optically active epoxy ester (formula 5) as the starting material, are described.

(formula 5)

Here, $R_1$ and $R_2$ denote straight-chain or branched alkyl groups containing 1 through 20 carbon atoms. * denotes asymmetric carbon atoms.

In the methods of preparing, alcohol is added to epoxy ester (formula 5) in the presence of a hydrolase in an organic solvent so as to de-esterify (−)-form of epoxy ester preferentially to be epoxy alcohol (formula 4).

(formula 4)

Here, $R_1$ and $R_2$ denote straight-chain or branched alkyl groups containing 1 through 20 carbon atoms.

Among the examples of epoxy ester (formula 5), especially carboxylate of 2,3-epoxy-8-methyl-1-nonanol is favorably used because (−)optically acive substance is useful as the synthetic intermediate of sex pheromone for injurious insects in forests (Lymantria dispar L).

In this raction, the enzyme to be used is a lipase like a lipase derived from pancrea of pig, yeast, mold, and a esterase like a esterase derived from lever of pig, a cholesterolesterase as same as above-mentioned reaction. Either purified or crude enzymes is not particularly restricted on use.

Moreover, the form is not particularly restricted and it is possible to re-use the enzyme after the reaction.

As for the organic solvent, all of non-aqueous system solvents can be used like the before-mentioned reaction, for example, an acyclic hydrocarbon solvent, a cyclic hydrocarbon solvent, a halogenated hydrocarbon solvent, an aromatic hydrocarbon solvent, an ether group solvent and carbon tetrachloride are favorably used.

Any alcohol is not restricted on use but branched or straight-chain alcohol containing about 1 through 10 carbon atoms are favorably used, for example, methanol, ethanol, n-propanol, iso-propanol, n-butanol, sec-butanol, etc.

The combination ratio of epoxy alcohol (formula 5) and alcohol is 1: not less than 1 in mole ratio.

The reaction temperature in this reaction is preferably within active temperature for enzymes, and ordinaly it is the range of 5° C. to 50° C.

After this de-esterifying reaction, the optically active substance, that is, optically active (−)-epoxy alcohol (formula 4) and optically active (+)-epoxy ester (formula 6) are separated from the reaction mixture.

(formula 6)

Here, $R_1$ and $R_2$ denote straight-chain or branched alkyl groups containing 1 through 20 carbon atoms.

There is no restriction on the separating process. As same as above-mentioned reaction, the extraction by using two layers system, the separation by using column and the separation by using distillaction etc. are favorably used.

As the preparations of optically active epoxy alcohol relating to this invention comprise of above-mentioned descriptions, it is effective to obtain optically active substance in high optical purity more than 80% e.e easily and extremely safely at ordinary temperature.

Hereinafter, this invention will be described more concretely accorindg to the detailed Examples.

EXAMPLE 1

Toluene (50 ml), 2,3-epoxy-8-methyl-1-nonanol (5 g), and acetic anhydride (2 g) were mixed in a 100 ml Mayer flask.

Lipase originated from pig pancreas (5 g) [Trade name: Pancreatin F, Maker: Amano Pharmaceutical] was added to the mixed solution and stirred with a magnetic stirrer at 25° C. for four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 3.2 g of (−)-(2S,3R)-1-acyloxy-2,3-epoxy-8-methylnonane (optical purity: 75% e.e), and 2.3 g of (+)-(2R,3S)-2,3-epoxy-8-methyl-1-nonanol (optical purity: 85% e.e).

Figure 1:
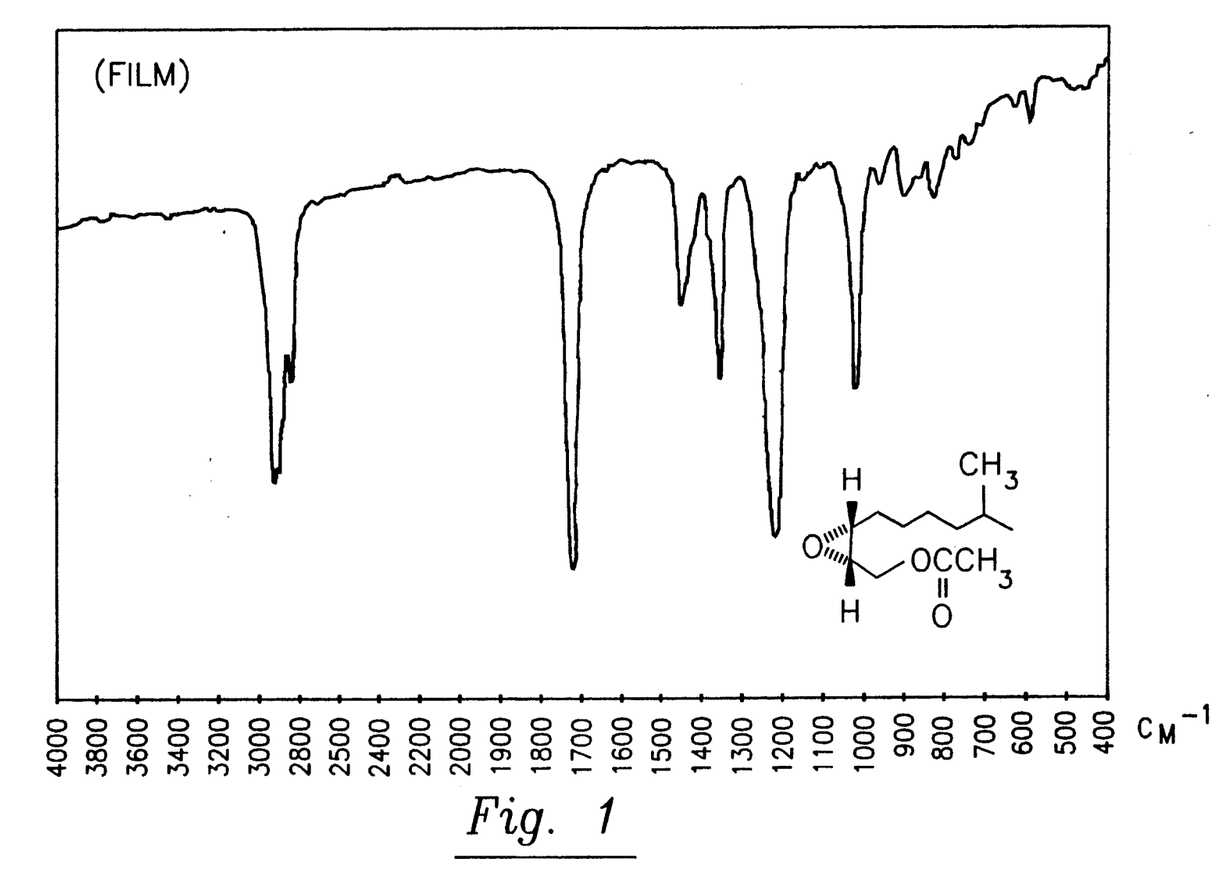
FIG. 1 is a infrared absorption spectral atlas of (−)-(2S,3R)-1-acyloxy-2,3-epoxy-8-methylnonane.

The infrared absorption spectra of (−)-(2S,3R)-1-acyloxy-2,3-epoxy-8-methylnonane showed the absorption at wavelengths (cm$^{-1}$) of 2,950(s), 2,930(s), 2,860(s), 1,740(s), 1,460(m), 1,360(m), 1,230(s), and 1,030(s) (see FIG. 1).

Figure 2:
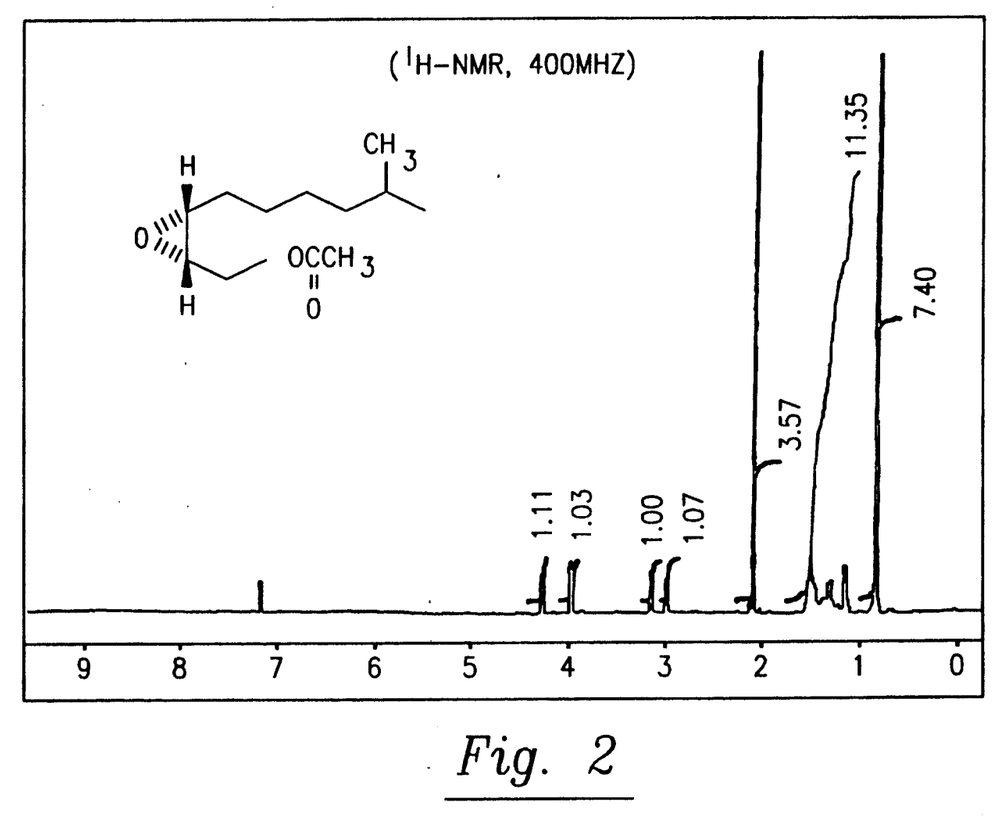
FIG. 2 is a proton nuclear magnetic resonance spectral atlas of (−)-(2S,3R)-1-acyloxy-2,3-epoxy-8-methylnonane.
Figure 3:
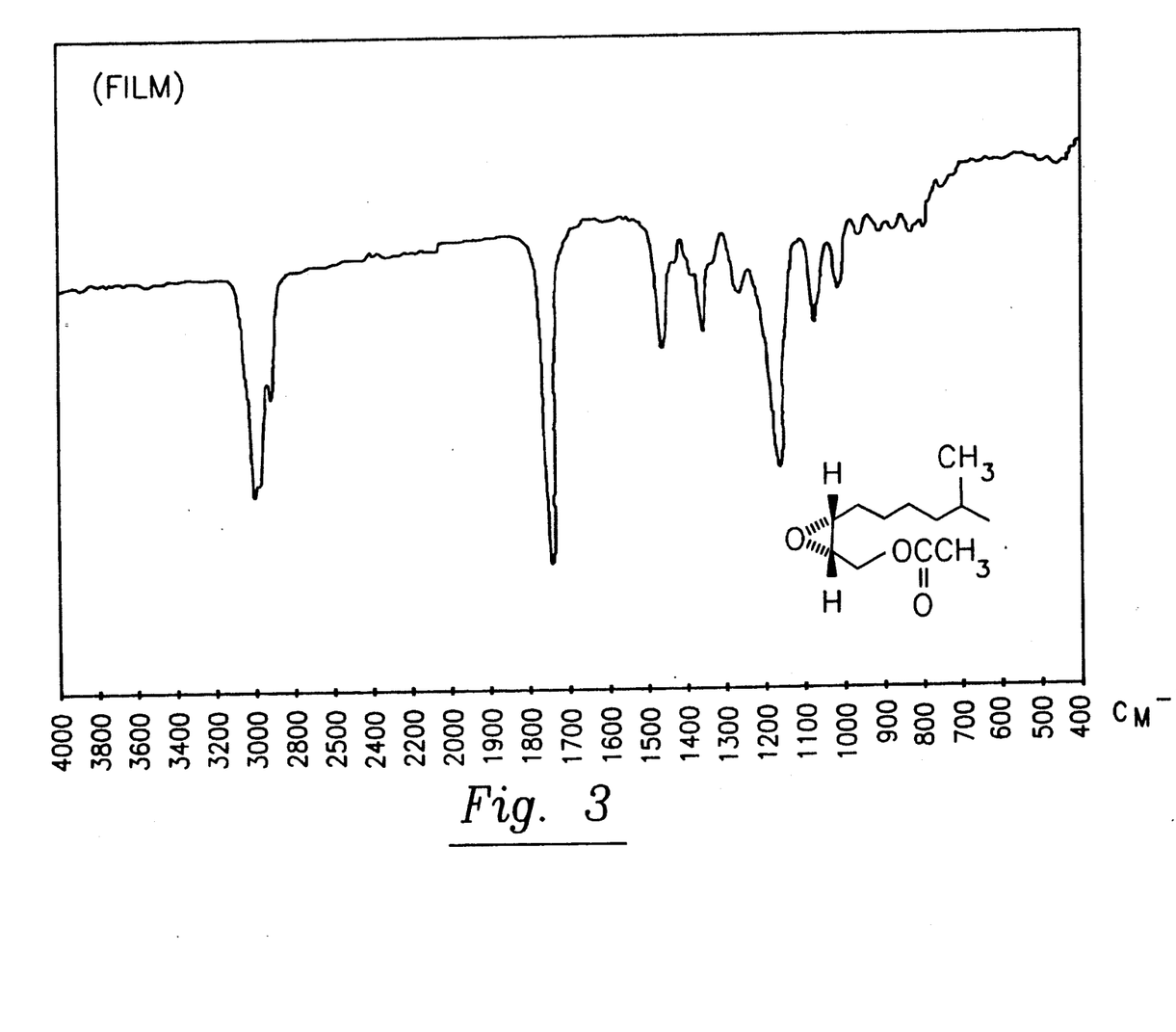
FIG. 3 is a infrared absorption spectral atlas of (−)-(2S,3R)-1-propynyloxy-2,3-epoxy-8-methylnonane.

The $\delta$ values of the proton nuclear magnetic resonance spectra $^1$H-NMR (CDCl$_3$, 400 MHz) were 0.85 (6H, d, J=6.9 Hz), 1.13 through 1.54 (9H, m), 2.08 (3H, s), 2.99 (1H, m), 3.15 (1H, m), 4.01 (1H, m), and 4.30 (1H, m) (see FIG. 2).

3.2 g of (−)-(2S,3R)-1-acyloxy-2,3-epoxy-8-methylnonane was hydrolyzed with potassium hydroxide/methanol to yield 2.4 g of (−)-(2S,3R)-2,3-epoxy-8-methyl-1-nonanol.

Benzoyl chloride was added to the compound to give benzoyl ester. Then the optical purity thereof was measured with an HPLC column for optical separation [Trade name: chiralcel OJ by Dicell Chemical Industries] (other examples were also measured in the same manner).

EXAMPLE 2

Toluene (50 ml), 2,3-epoxy-8-methyl-1-nonanol (5 g), and propionic anhydride (2 g) were mixed in a 100 ml Mayer flask.

Lipase originated from pig pancreas (5 g) [Trade name: Pancreatin F, Maker: Amano Pharmaceutical] was added to the mixed solution and stirred with a magnetic stirrer at 25° C. for four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 3.4 g of (−)-(2S,3R)-1-propionyloxy-2,3-epoxy-8-methylnonane (optical purity: 80% e.e), and 2.2 g of (+)-(2R,3S)-2,3-epoxy-8-methyl-1-nonanol (optical purity: 88% e.e).

Figure 4:
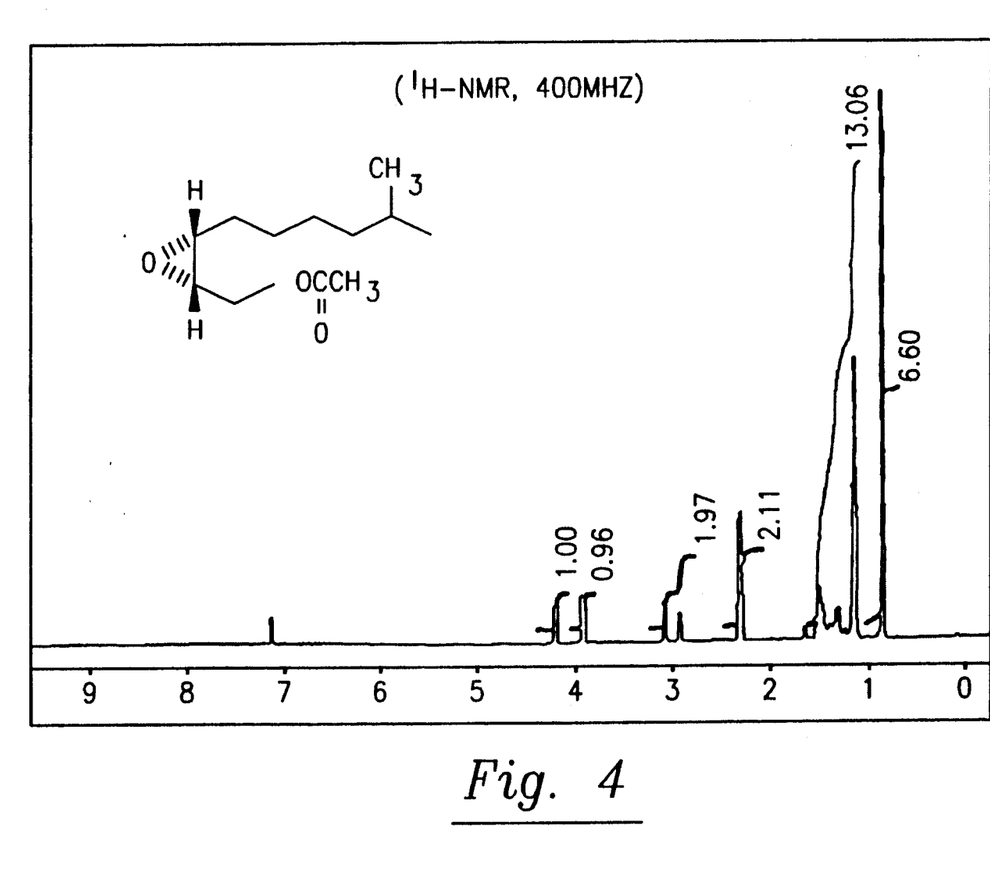
FIG. 4 is a proton nuclear magnetic resonance spectral atlas of (−)-(2S,3R)-1-propynyloxy-2,3-epoxy-8-methylnonane.

The infrared absorption spectra of (−)-(2S,3R)-1-propionyloxy 2,3-epoxy-8-methylnonane showed the absorption at wavelengths (cm$^{-1}$) of 2,950(s), 2,920(s), 2,850(s), 1,740(s), 1,460(m), 1,360(m), 1,180(s), and 1,080(s) (see FIG. 4).

The $\delta$ values of the proton nuclear magnetic resonance spectra $^1$H-NMR (CDCl$_3$, 400 MHz) were 0.84 (6H, d, J=6.9 Hz), 1.12 through 1.54 (12H, m), 2.36 (2H, q, J=7.6 Hz), 2.98 (1H, m), 3.14 (1H, m), 4.02 (1H, m), and 4.30 (1H, m), (see FIG. 4).

3.4 g of (−)-(2S,3R)-1-propionyloxy-2,3-epoxy-8-methylnonane was hydrolyzed with potassium hydroxide/methanol to yield 2.4 g of (−)-(2S,3R)-2,3-epoxy-8-methyl-1-nonanol.

EXAMPLE 3

Toluene (50 ml), 2,3-epoxy-8-methyl-1-nonanol (5 g), and n-butyric acid anhydride (3 g) were mixed in a 100 ml Mayer flask.

Lipase originated from pig pancreas (5 g) [Trade name: Pancreatin F, Maker: Amano Pharmaceutical] was added to the mixed solution and stirred with a magnetic stirrer at 25° C. for three hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 3.6 g of (−)-(2S,3R)-1-butyroxy-2,3-epoxy-8-methylnonate (optical purity: 89% e.e), and 2.2 g of (+)-(2R,3S)-2,3-epoxy-8-methyl-1-nonanol (optical purity: 91% e.e).

Figure 5:
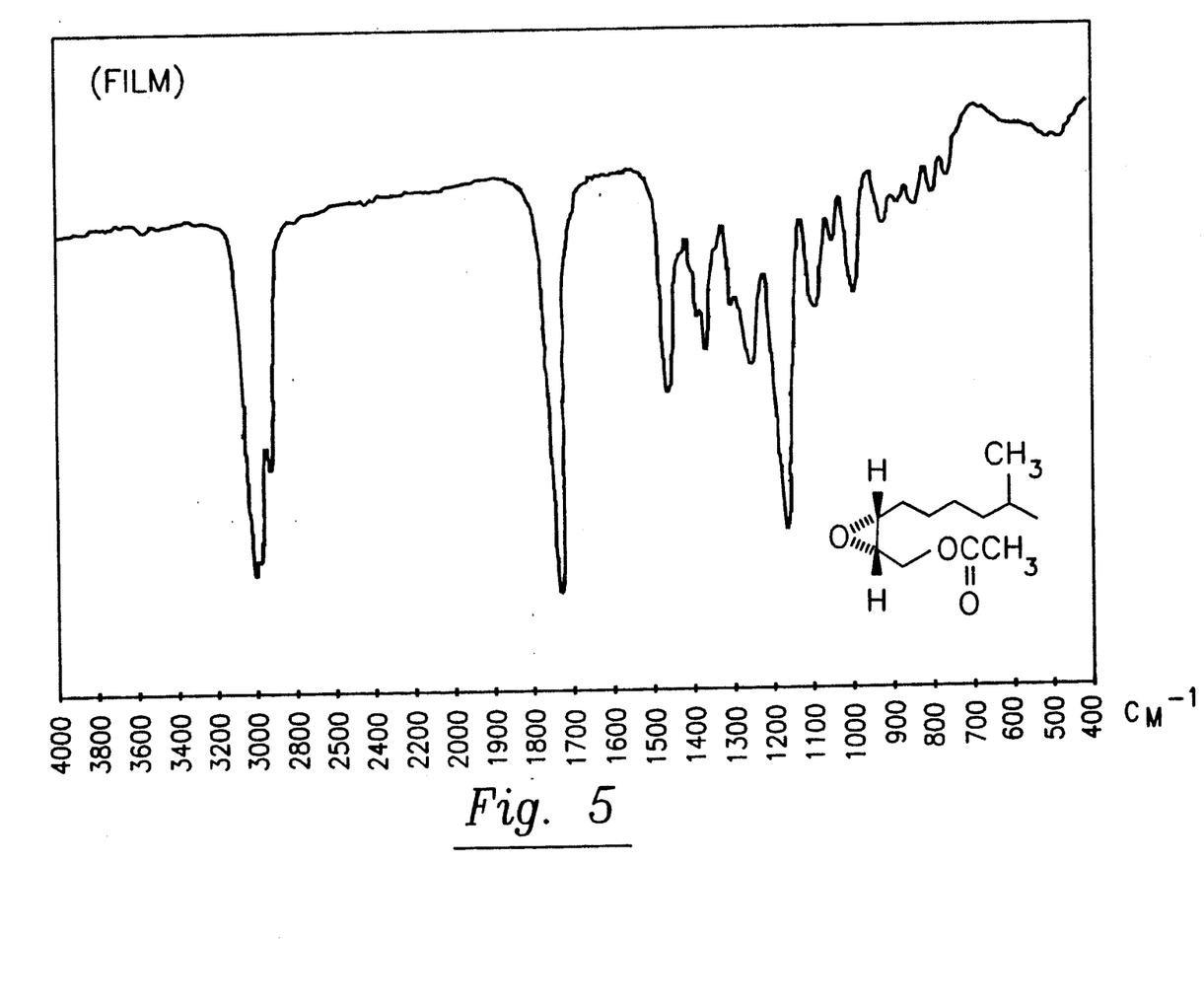
FIG. 5 is a infrared absorption spectral atlas of (−)-(2S,3R)-1-capryloxy-2,3-epoxy-8-methylnonane.

The infrared absorption spectra of (−)-(2S,3R)-1-butyroxy 2,3-epoxy-8-methylnonane showed the absorption at wavelengths (cm$^{-1}$) of 2,950(s), 2,930(s), 2,860(s), 1,740(s), 1,460(m), 1,360(m), 1,180(s), and 1,080(w) (see FIG. 5).

Figure 6:
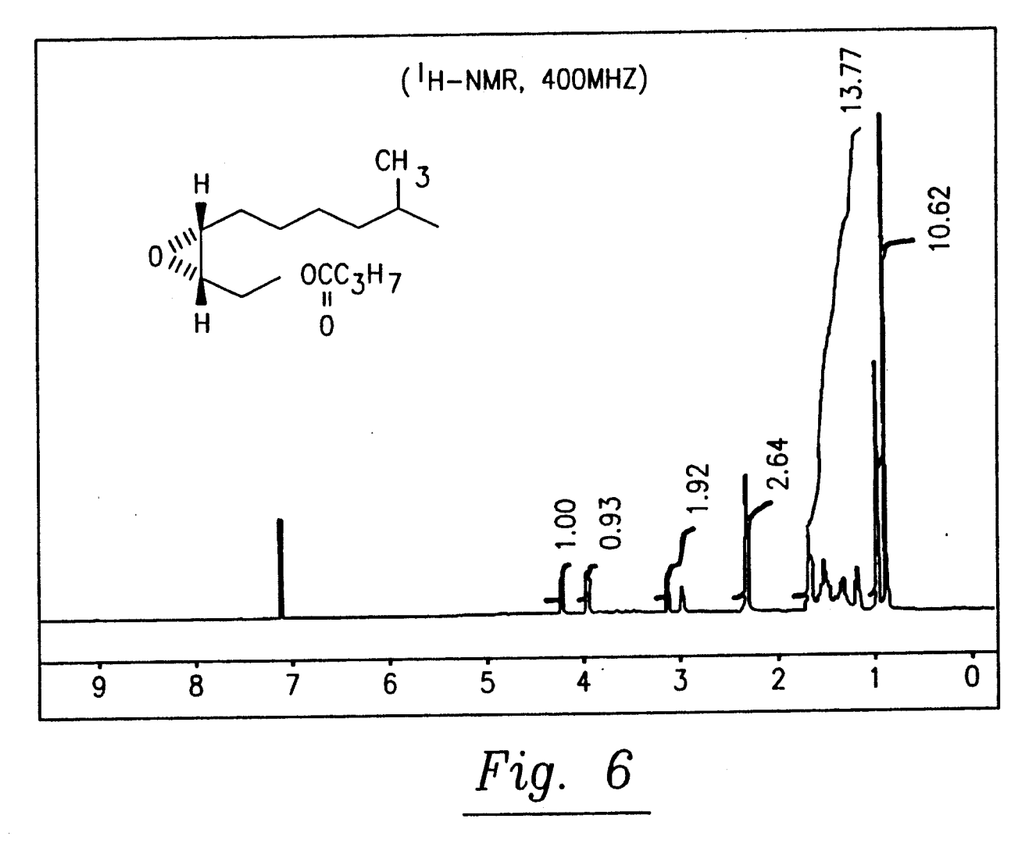
FIG. 6 is a proton nuclear magnetic resonance spectral atlas of (−)-(2S,3R)-1-capryloxy-2,3-epoxy-8-methylnonane.

The $\delta$ values of the proton nuclear magnetic resonance spectra $^1$H-NMR (CDCl$_3$, 400 MHz) were 0.85 (6H, d, J=4.9 Hz), 0.94 (3H, t, J=2.7 Hz), 1.14 through 1.69 (11H, m), 2.33 (3H, d, J=7.3 Hz), 2.99 (1H, m), 3.16 (1H, m), 4.03 (1H, m), and 4.31 (1H, m) (see FIG. 6).

3.6 g of (−)-(2S,3R)-1-butyroxy-2,3-epoxy-8-methylnonane was hydrolyzed with potassium hydroxide/methanol to yield 2.4 g of (−)-(2S,3R)-2,3-epoxy-8-methyl-1-nonanol.

EXAMPLE 4

Toluene (50 ml), 2,3-epoxy-8-methyl-1-nonanol (5 g), and n-valeric acid anhydride (3.2 g) were mixed in a 100 ml Mayer flask.

Lipase originated from pig pancreas (5 g) [Trade name: Pancreatin F, Maker: Amano Pharmaceutical] was added to the mixed solution and stirred with a magnetic stirrer at 25° C. for three hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 3.8 g of (−)-(2S, 3R)-1-valeroxy-2,3-epoxy-8-methylnonane (optical purity: 90% e.e), and 2.2 g of (+)-(2R, 3S)-2,3-epoxy-8-methyl-1-nonanol (optical purity: 92% e.e.).

Figure 7:
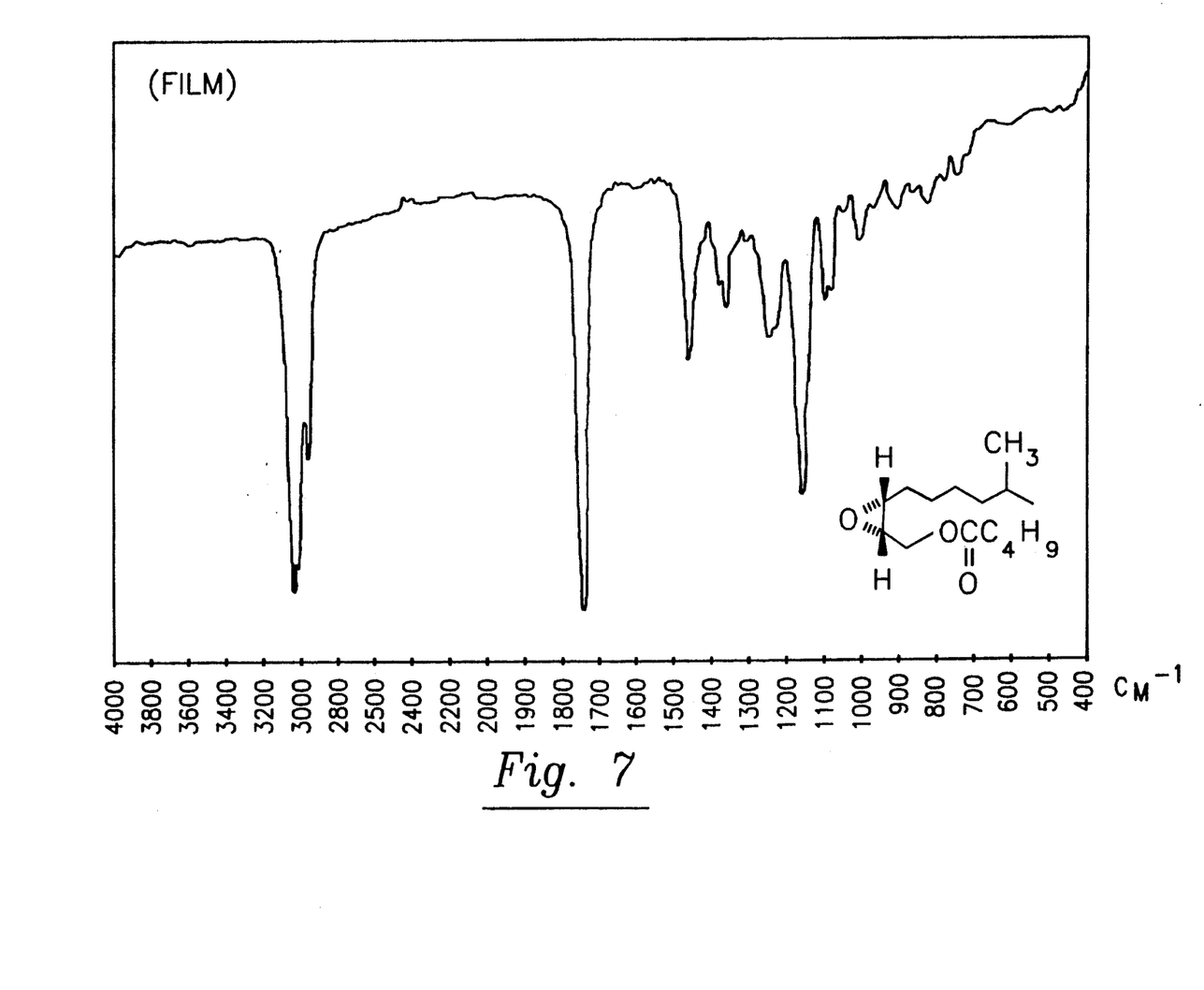
FIG. 7 is a infrared absorption spectral atlas of (−)-(2S,3R)-1-valeroxy-2,3-epoxy-8-methylnonane.

The infrared absorption spectra of (−)-(2S, 3R)-1-valeroxy 2,3-epoxy-8-methylnonane showed the absorption at wavelengths (cm$^{-1}$) of 2,950(s), 2,930(s), 2,850(s), 1,740(s), 1,460(m), 1,360(w), 1,160(s), and 1,100(w) (see FIG. 7).

Figure 8:
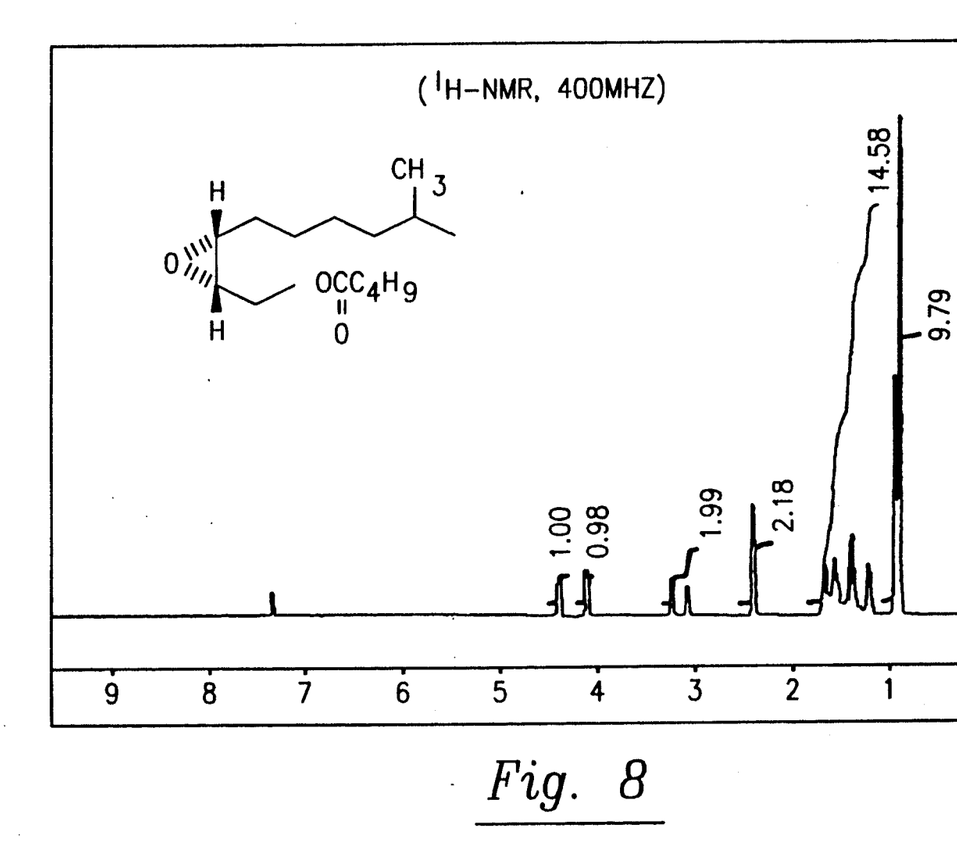
FIG. 8 is a proton nuclear magnetic resonance spectral atlas of (−)-(2S,3R)-1-valeroxy-2,3-epoxy-8-methylnonane.

The δ values of the proton nuclear magnetic resonance spectra $^1$H-NMR (CDCl$_3$, 400 MHz) were 0.85 (6H, d, J=6.6 Hz), 0.90 (3H, t, J=7.3 Hz), 1.13 through 1.64 (13H, m), 2.34 (2H, t, J=7.3 Hz), 2.98 (1H, m), 3.15 (1H, m), 4.02 (1H, m), and 4.29 (1H, m) (see FIG. 8).

3.8 g of (−)-(2S, 3R)-1-valeroxy-2,3-epoxy-8-methylnonane was hydrolyzed with potassium hydroxide/methanol to yield 2.3 g of (−)-(2S, 3R)-2,3-epoxy-8-methyl-1-nonanol.

EXAMPLE 5

Toluene (50 ml), 2,3-epoxy-8-methyl-1-nonanol (5 g), and n-caproic acid anhydride (3.2 g) were mixed in a 100 ml Mayer flask.

Lipase originated from pig pancreas (5 g) [Trade name: Pancreatin F, Maker: Amano Pharmaceutical] was added to the mixed solution and stirred with a magnetic stirrer at 25° C. for three hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 4.1 g of (−)-(2S, 3R)-1-capryloxy-2,3-epoxy-8-methylnonane (optical purity: 90% e.e.), and 2.2 g of (+)-(2R, 3S)-2,3-epoxy-8-methyl-1-nonanol (optical purity: 92% e.e).

Figure 9:
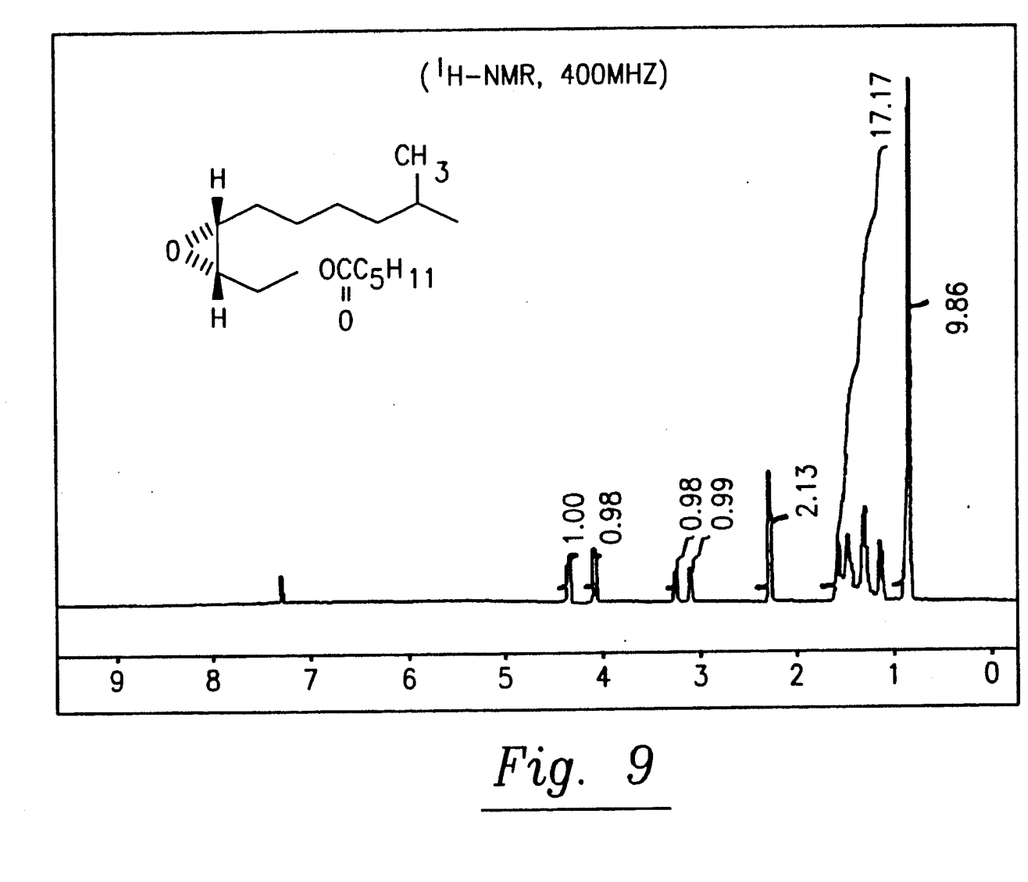
FIG. 9 is a infrared absorption spectral atlas of (−)-(2S,3R)-1-capryloxy-2,3-epoxy-8-methylnonane.

The infrared absorption spectra of (−)-(2S, 3R)-1-capryloxy 2,3-epoxy-8-methylnonane showed the absorption at wavelengths (cm$^{-1}$) of 2,950(s), 2,920(s), 2,850(s), 1,740(s), 1,460(m), 1,360(w), 1,160(s), and 1,100(w) (see FIG. 9).

Figure 10:
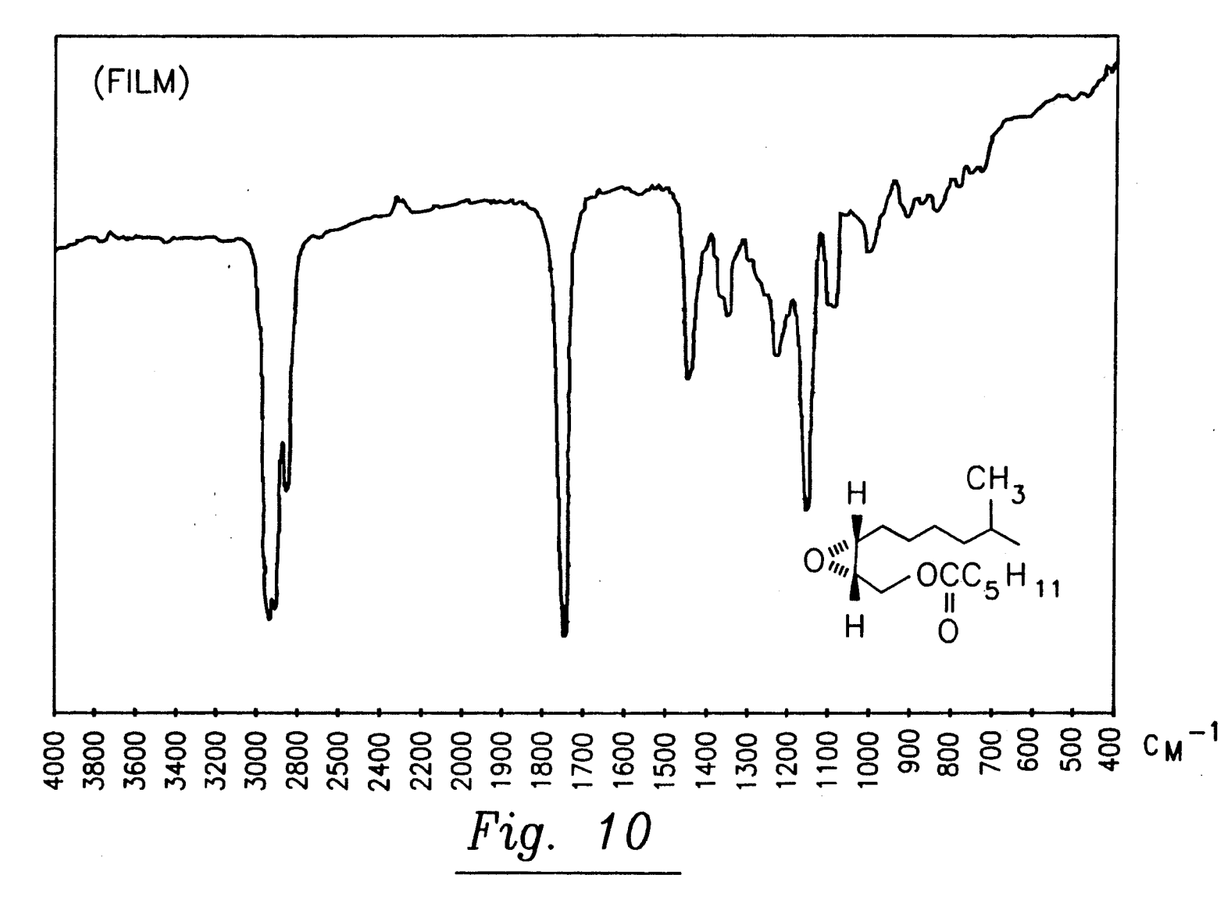
FIG. 10 is a proton nuclear magnetic resonance spectral atlas of (−)-(2S,3R)-1-capryloxy-2,3-epoxy-8-methylnonane.

The δ values of the proton nuclear magnetic resonance spectra $^1$H-NMR (CDCl$_3$, 400 MHz) were 0.85 (6H, d, J=6.6 Hz), 0.88 (3H, t, J=6.8 Hz), 1.13 through 1.64 (15H, m), 2.34 (2H, t, J=7.3 Hz), 2.99 (1H, m), 3.15 (1H, m), 4.02 (1H, m), and 4.30 (1H, m) (see FIG. 10).

4.1 g of (−)-(2S, 3R)-1-capryloxy-2,3-epoxy-8-methylnonane was hydrolyzed with potassium hydroxide/methanol to yield 2.3 g of (−)-(2S, 3R)-2,3-epoxy-8-methyl-1-nonanol.

EXAMPLE 6

Isopropyl ester (50 ml), 1-acetoxy-2,3-epoxy-8-methylnonane (1 g), and methanol (5 g) were mixed in a 100 ml Mayer flask.

Lipase originated from pig pancreas (1 g) [Trade name: Pancreatin F, Maker: Amano Pharmaceutical] was added to the mixed solution and stirred with a magnetic stirrer at 25° C. for twenty-four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 1.7 g of (−)-(2S, 3R)-2,3-epoxy-8-methyl-1-nonanol (optical purity: 82% e.e), and 2.5 g of (+)-(2R, 3S)-1-acetoxy-2,3-epoxy-8-methylnonane (optical purity: 70% e.e).

Figure 11:
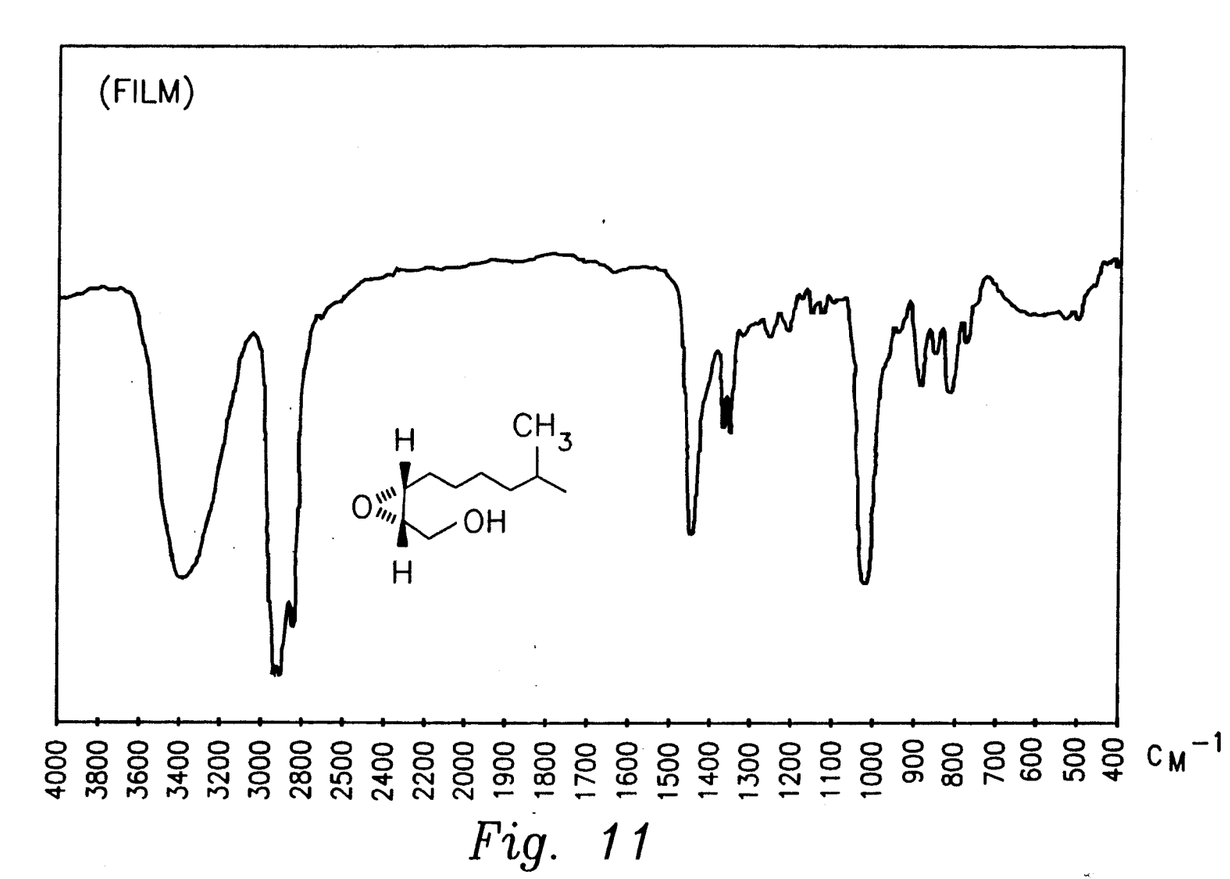
FIG. 11 is a infrared absorption spectral atlas of (−)-(2S,3R)-2,3-epoxy-8-methyl-1-nonanol.
Figure 12:
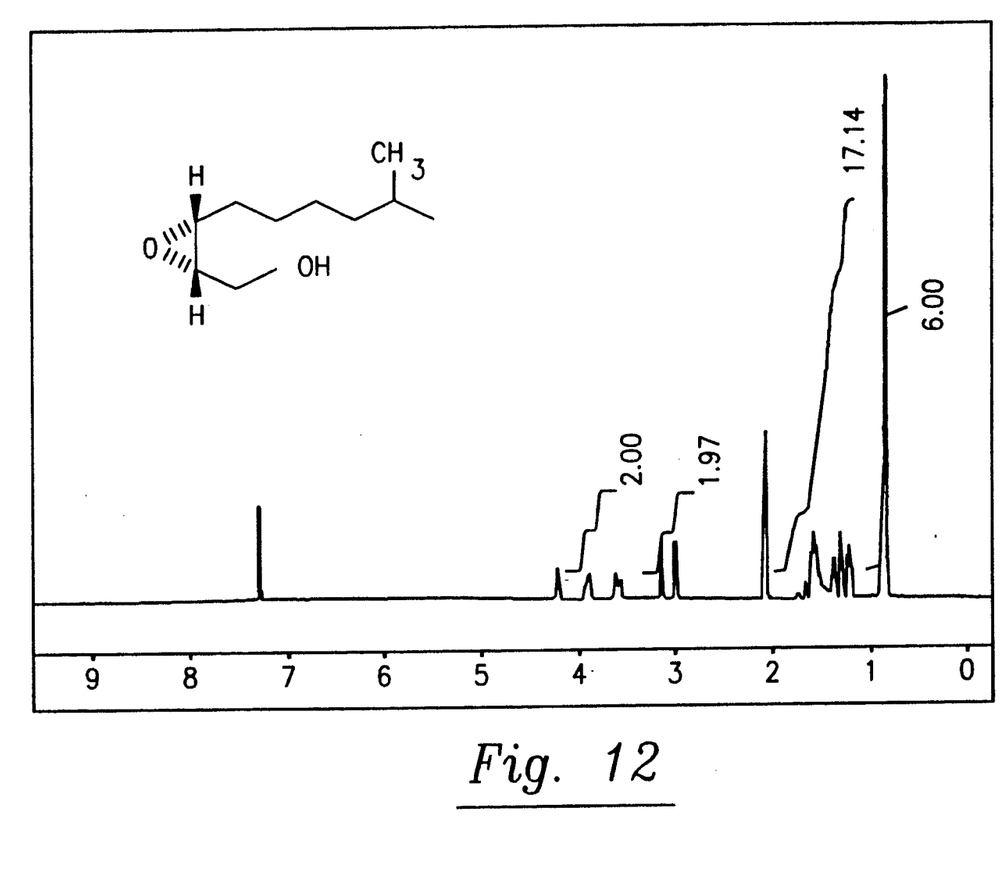
FIG. 12 is a proton nuclear magnetic resonance spectral atlas of (−)-(2S,3R)-2,3-epoxy-8-methyl-1-nonanol.

And, (−)-(2S, 3R)-2,3-epoxy-8-methyl-1-nonanol was identified by infrared absorption spectra and proton nuclear magnetic resonance spectra (see FIG. 11 and FIG. 12).

EXAMPLE 7

Isopropyl ester (50 ml), 1-acetoxy-2,3-epoxy-8-methylnonane (1 g), and n-propanol (5 g) were mixed in a 100 ml Mayer flask.

Lipase originated from pig pancreas (1 g) [Trade name: Pancreatin F, Maker: Amano Pharmaceutical] was added to the mixed solution and stirred with a magnetic stirrer at 25° C. for twenty-four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 1.6 g of (−)-(2S, 3R)-2,3-epoxy-8-methyl-1-nonanol (optical purity: 80% e.e), and 2.5 g of (+)-(2R, 3S)-1-acetoxy-2,3-epoxy-8-methylnonane (optical purity: 71% e.e).

And, (−)-(2S, 3R)-2,3-epoxy-8-methyl-1-nonanol was identified by infrared absorption spectra and proton nuclear magnetic resonance spectra as in Example 6.

EXAMPLE 8

Isopropyl ester (50 ml), 1-acetoxy-2,3-epoxy-8-methylnonane (1 g), and ethanol (5 g) were mixed in a 100 ml Mayer flask.

Lipase originated from pig pancreas (1 g) [Trade name: Pancreatin F, Maker: Amano Pharmaceutical] was added to the mixed solution and stirred with a magnetic stirrer at 25° C. for twenty-four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 1.6 g of (−)-(2S, 3R)-2,3-epoxy-8-methyl-1-nonanol (optical purity: 81% e.e), and 2.7 g of (+)-(2R, 3S)-1-acetoxy-2,3-epoxy-8-methylnonane (optical purity: 70% e.e).

And, (−)-(2S, 3R)-2,3-epoxy-8-methyl-1-nonanol was identified by infrared absorption spectra and proton nuclear magnetic resonance spectra as in Example 6.

EXAMPLE 9

Isopropyl ester (50 ml), 1-acetoxy-2,3-epoxy-8-methylnonane (1 g), and n-butanol (5 g) were mixed in a 100 ml Mayer flask.

Lipase originated from pig pancreas (1 g) [Trade name: Pancreatin F, Maker: Amano Pharmaceutical] was added to the mixed solution and stirred with a magnetic stirrer at 25° C. for twenty-four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 1.5 g of (−)-(2S, 3R)-2,3-epoxy-8-methyl-1-nonanol (optical purity: 84% e.e), and 2.6 g of (+)-(2R, 3S)-1-acetoxy-2,3-epoxy-8-methyl-1-nonanol (optical purity: 65% e.e).

And, (−)-(2S, 3R)-2,3-epoxy-8-methyl-1-nonanol was identified by infrared absorption spectra and proton nuclear magnetic resonance spectra as in Example 6.

EXAMPLE 10

Isopropyl ester (50 ml), 1-propionyloxy-2,3-epoxy-8-methylnonane (1 g), and methanol (5 g) were mixed in a 100 ml Mayer flask.

Lipase originated from pig pancreas (1 g) [Trade name: Pancreatin F, Maker: Amano Pharmaceutical] was added to the mixed solution and stirred with a magnetic stirrer at 25° C. for twenty-four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 1.6 g of (−)-(2S, 3R)-2,3-epoxy-8-methyl-1-nonanol (optical purity: 82% e.e), and 2.6 g of (+)-(2R, 3S)-1-propionyloxy-2,3 epoxy-8-methylnonane (optical purity: 68% e.e).

And, (−)-(2S, 3R)-2,3-epoxy-8-methyl-1-nonanol was identified by infrared absorption spectra and proton nuclear magnetic resonance spectra as in Example 6.

EXAMPLE 11

Isopropyl ester (50 ml), 1-butanoyloxy-2,3-epoxy-8-methylnonane (1 g), and methanol (5 g) were mixed in a 100 ml Mayer flask.

Lipase originated from pig pancreas (1 g) [Trade name: Pancreatin F, Maker: Amano Pharmaceutical] was added to the mixed solution and stirred with a magnetic stirrer at 25° C. for twenty-four hours for conclusion of the reaction.

After the solution was filtered, the filtrate was concentrated with a rotary evaporator and the solvent was removed.

The oily substance thus obtained was separated by silica gel column chromatography with hexane/ethyl acetate as eluate to yield 1.6 g of (−)-(2S, 3R)-2,3-epoxy-8-methyl-1-nonanol (optical purity: 82% e.e), and 2.8 g of (+)-(2R, 3S)-1-butanoyloxy-2,3-epoxy-8-methyl-1-nonanol (optical purity: 68% e.e).

And, (−)-(2S, 3R)-2,3-epoxy-8-methyl-1-nonanol was identified by infrared absorption spectra and proton nuclear magnetic resonance spectra as in Example 6.

What is claimed is:

1. A method of preparing optically active epoxy alcohol, comprising the steps of:

adding carboxylic anhydride to racemic epoxy alcohol (formula 1) in the presence of lipase in an organic solvent;

esterifying (−)-form of the epoxy alcohol preferentially to give epoxy ester (formula 2);

separating optically active epoxy ester (formula 2) from optically active epoxy alcohol (formula 3); and hydrolyzing said optically active epoxy ester (formula 2) to yield optically active epoxy alcohol (formula 4);

(formula 1)

(formula 2)

(formula 3)

(formula 4)

where $R_1$ and $R_2$ denote straight-chain or branched alkyl groups containing 1 through 20 carbon atoms, and where * denotes asymmetric carbon atoms;

whereby said optically active epoxy alcohol is synthesized in two steps, a first step being a hydrolase enzyme reaction to prepare optically active esters from racemic alcohol and whereby a second step is a hydrosis chemical reaction to prepare optically active alcohol from said optically active esters.

2. The method of preparing optically active epoxy alcohol, in accordance with claim 1, wherein said epoxy alcohol (formula 1) is 2,3-epoxy-8-methyl-1-nonanol.

3. The method of preparing optically active epoxy alcohol, in accordance with claim 1, wherein said epoxy alcohol (formula 4) is 2,3-epoxy-8-methyl-1-nonanol.

4. A method of preparing optically active epoxy alcohol, comprising the steps of:

adding alcohol to epoxy ester of the formula 5

(formula 5)

where $R_1$ and $R_2$ denote straight-chain or branched alkyl groups containing 1 through 20 carbon atoms, and where * denotes asymmetric carbon atoms;

in the presence of a lipase in an organic solvent;

de-esterifying (−)-form of the epoxy ester preferentially to give epoxy alcohol of the formula 4

(formula 4)

where $R_1$ and $R_2$ denote straight-chain or branched alkyl groups containing 1 through 20 carbon atoms;

and, separating said epoxy alcohol from epoxy ester of formula 6

(formula 6)

where $R_1$ and $R_2$ denote straight-chain or branched alkyl groups containing 1 through 20 carbon atoms.

5. The method of preparing optically active epoxy alcohol, in accordance with claim 4 wherein said epoxy ester (formula 5) is carboxylic ester of 2,3-epoxy-8-methyl-1-nonanol containing 1 through 10 carbon atoms.

* * * * *